United States Patent
Nebuya

(10) Patent No.: US 11,647,951 B2
(45) Date of Patent: May 16, 2023

(54) INPUT DEVICE, FIBER SHEET, CLOTHING, AND BIOLOGICAL INFORMATION DETECTION DEVICE

(71) Applicant: SCHOOL JURIDICAL PERSON KITASATO INSTITUTE, Tokyo (JP)

(72) Inventor: Satoru Nebuya, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 702 days.

(21) Appl. No.: 15/121,529

(22) PCT Filed: Feb. 27, 2015

(86) PCT No.: PCT/JP2015/055941
§ 371 (c)(1),
(2) Date: Oct. 31, 2016

(87) PCT Pub. No.: WO2015/129887
PCT Pub. Date: Sep. 3, 2015

(65) Prior Publication Data
US 2017/0164896 A1    Jun. 15, 2017

(30) Foreign Application Priority Data

Feb. 28, 2014   (JP) .............................. JP2014-039885

(51) Int. Cl.
*A61B 5/00*    (2006.01)
*A61B 5/0245*    (2006.01)
(Continued)

(52) U.S. Cl.
CPC .............. *A61B 5/6804* (2013.01); *A41B 1/08* (2013.01); *A61B 5/0245* (2013.01);
(Continued)

(58) Field of Classification Search
CPC ... A61B 5/6804; A61B 5/02438; A61B 5/085; A61B 5/0535; A61B 5/0245;
(Continued)

(56) References Cited

U.S. PATENT DOCUMENTS

2002/0032383 A1    3/2002   Weil et al.
2004/0111041 A1*   6/2004   Ni .......................... A61N 1/365
                                                                   607/9

(Continued)

FOREIGN PATENT DOCUMENTS

JP    11-168268    6/1999
JP    2000-14655   1/2000
(Continued)

OTHER PUBLICATIONS

Extended European Search Report issued in Appln. No. 15755819.8 dated Oct. 16, 2017.
(Continued)

*Primary Examiner* — Adam Z Minchella
(74) *Attorney, Agent, or Firm* — Nixon & Vanderhye PC

(57) ABSTRACT

An input device includes two conductors that are sewn onto a fiber sheet and an output unit configured to determine an impedance variation in a predetermined area on the basis of a voltage value between the two conductors to which a high-frequency current is applied.

16 Claims, 8 Drawing Sheets

(51) Int. Cl.
  *A61B 5/113* (2006.01)
  *A61B 5/0295* (2006.01)
  *A61B 5/0535* (2021.01)
  *A61B 5/11* (2006.01)
  *A41B 1/08* (2006.01)
  *A61B 5/024* (2006.01)
  *A61B 5/08* (2006.01)
  *A61N 1/04* (2006.01)

(52) U.S. Cl.
  CPC ........ *A61B 5/0295* (2013.01); *A61B 5/02438* (2013.01); *A61B 5/0535* (2013.01); *A61B 5/0809* (2013.01); *A61B 5/1102* (2013.01); *A61B 5/113* (2013.01); *A61B 5/0816* (2013.01); *A61B 2562/0214* (2013.01); *A61B 2562/164* (2013.01); *A61B 2562/182* (2013.01); *A61N 1/0484* (2013.01)

(58) Field of Classification Search
  CPC ... A61B 5/0295; A61B 5/0809; A61B 5/1102; A61B 5/113; A61B 5/0816; A61B 2562/0214; A61B 2562/164; A61B 2562/182; A41B 1/08; A61N 1/0484
  See application file for complete search history.

(56) References Cited

U.S. PATENT DOCUMENTS

| | | | | |
|---|---|---|---|---|
| 2005/0054941 | A1* | 3/2005 | Ting | A61B 5/296 600/534 |
| 2006/0111640 | A1* | 5/2006 | Shen | A61B 5/0006 600/509 |
| 2008/0183095 | A1* | 7/2008 | Austin | A61B 5/0809 600/534 |
| 2008/0218180 | A1* | 9/2008 | Waffenschmidt | A61B 5/6887 324/633 |
| 2009/0088652 | A1* | 4/2009 | Tremblay | A61B 5/6804 600/389 |
| 2009/0281394 | A1 | 11/2009 | Russell et al. | |
| 2010/0298899 | A1* | 11/2010 | Donnelly | A61N 1/3987 607/6 |
| 2012/0101357 | A1 | 4/2012 | Hoskuldsson et al. | |
| 2012/0215076 | A1 | 8/2012 | Yang et al. | |
| 2013/0066168 | A1 | 3/2013 | Yang et al. | |
| 2013/0197387 | A1* | 8/2013 | Lipoma | A61B 5/1126 600/595 |
| 2014/0318699 | A1* | 10/2014 | Longinotti-Buitoni | A61B 5/743 156/247 |

FOREIGN PATENT DOCUMENTS

| | | |
|---|---|---|
| JP | 2005-253610 | 9/2005 |
| JP | 2005-322052 | 11/2005 |
| JP | 2007-201641 | 8/2007 |
| JP | 2009-244020 | 10/2009 |
| JP | 2011-86114 | 4/2011 |
| JP | 2012-90880 | 5/2012 |
| JP | 2013-63186 | 4/2013 |
| JP | 2013-81577 | 5/2013 |
| JP | 2014-502181 | 1/2014 |
| JP | 2014-233619 | 12/2014 |
| WO | 2005/032368 | 4/2005 |
| WO | WO 2010/038176 | 4/2010 |
| WO | WO-2010038176 A1 * | 4/2010 ........... A61B 5/0537 |

OTHER PUBLICATIONS

International Search Report issued in PCT/JP2015/055941 dated May 26, 2015.
Office Action issued in JP Appln. No. 2016-505338 dated Feb. 26, 2019 (w/ translation).
Search Report issued in EP Appln. No. 20153537.4 dated Aug. 24, 2020.
Fredd Alferink, "Measuring capacitance:: Electronic Measurements", Informationstechnik, Jan. 20, 2014, pp. 1-6, XP055653416, Retrieved from the Internet: URL: https://meettechniek.info/passive/capacitance.html [retrieved on Dec. 17, 2019].
Office Action issued in JP App. No. 2020-075681 (dated Mar. 9, 2021) (w/ translation).

* cited by examiner

INPUT DEVICE, FIBER SHEET, CLOTHING, AND BIOLOGICAL INFORMATION DETECTION DEVICE

This application is the U.S. national phase of International Application No. PCT/JP2015/055941 filed 27 Feb. 2015, which designated the U.S. and claims priority to JP Patent Application No. 2014-039885 filed 28 Feb. 2014, the entire contents of each of which are hereby incorporated by reference.

TECHNICAL FIELD

The present invention relates to an input device, a fiber sheet, an article of clothing, and a biological information detection device.

BACKGROUND

In some countries, the number of aged persons has increased, and many electrical devices that can be easily used by aged persons have been developed and sold. In order to reduce social costs accompanying the aging of citizens, it is preferable to promote better health care. In such circumstances, there is a need for an input device that can be easily used by aged persons. There is also a need for a device that can easily carry out health care. For example, relevant techniques are disclosed in Patent Document 1 and Patent Document 2.

RELATED ART DOCUMENTS

Patent Document

[Patent Document 1]
 Japanese Patent Application, Publication No. 2011-86114
[Patent Document 2]
 Japanese Patent Application, Publication No. 2005-322052

SUMMARY OF INVENTION

Technical Problem

Patent Document 1 discloses a technique of a conductive fabric having a folding structure that is devised to accurately detect a touched position.

Patent Document 2 discloses a technique relevant to conductive clothes and a device attached to a conductive fabric of the conductive clothes.

However, in the conductive fabric disclosed in Patent Document 1, an input operation cannot be performed unless a user actually touches the fabric. There is a need for a device that operates by detecting a measurement target in a contactless manner.

An object of an aspect of the present invention is to provide an input device, a fiber sheet, an article of clothing, and a biological information detection device that can be suitably used for contactless sensing or detection of biological information.

Solution to Problem

According to an aspect of the present invention, there is provided an article of clothing including: a cloth; at least two conductors that are set in the cloth; and an output unit configured to determine an impedance variation of a predetermined area on the basis of a voltage value between the at least two conductors to which a high-frequency current is applied.

According to another aspect of the present invention, there is provided a biological information detection device including: two first conductors that are set in an article of clothing; two second conductors that are set in the article of clothing at positions corresponding to lungs or a heart; an output unit configured to determine an impedance variation in an area in the vicinity of the two first conductors on the basis of a voltage value between the two first conductors to which a first high-frequency current is applied; and a biological information detection unit configured to determine biological information on the basis of a voltage value between the two second conductors to which a second high-frequency current is applied.

According to still another aspect of the present invention, there is provided a biological information detection device including: two conductors that are set in a cloth at positions corresponding to lungs or a heart; and a biological information detection unit configured to determine biological information on the basis of a voltage value between the two conductors to which a high-frequency current is applied.

According to still another aspect of the present invention, there is provided an input device including: two conductors that are sewn onto a fiber sheet; and an output unit configured to determine an impedance variation in a predetermined area on the basis of a voltage value between the two conductors to which a high-frequency current is applied.

According to still another aspect of the present invention, there is provided a fiber sheet including the above-mentioned input device.

Advantageous Effects of Invention

According to aspects of the present invention, it is possible to provide an input device, a fiber sheet, an article of clothing, and a biological information detection device which can be suitably used for contactless sensing or detection of biological information.

DESCRIPTION OF EMBODIMENTS

Hereinafter, an input device according to an embodiment of the present invention and a fiber sheet and an article of clothing to which the input device is added will be described with reference to the accompanying drawings.

Figure 1:
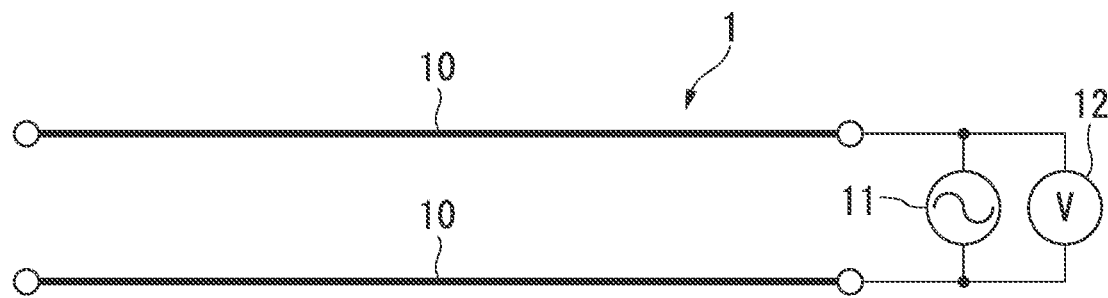
FIG. 1 is a diagram showing a configuration of an input device according to an embodiment of the present invention.
Figure 1:
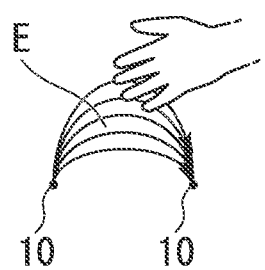

FIG. 1 is a diagram showing a configuration of an input device 1 according to an embodiment of the present invention.

In FIG. 1, reference numeral 10 denotes a linear conductor. For example, the conductor 10 is a conductive thread (electrode thread). The input device 1 shown in FIG. 1 includes two wire-shaped (thread-shaped) conductors (electrodes) 10. The two conductors 10 are disposed so as to be separated from each other. A substantial gap is formed between the two conductors 10. A high-frequency current (a first high-frequency current) is input to the input device 1 from a current source 11 (a first current input source, a first input source) connected to end points of the conductors 10. The input device 1 measures a voltage value across the end points of the conductors 10 using a voltage measuring unit 12. When a high-frequency current is input to the conductors 10, an electric field E is generated in a space between the two conductors 10 to which the high-frequency current is input. For example, when a hand is put into the electric field area, the electric field varies and the voltage value measured by the voltage measuring unit 12 varies. The input device 1 can normally monitor an impedance variation due to an influence of a measuring object (for example, a hand) put into a predetermined area (electric field area) in the vicinity of the conductors 10 on the basis of the variation in the voltage value using the voltage measuring unit 12 connected in parallel to the current source 11. The impedance value is acquired by dividing the voltage value by the current value. The input device 1 outputs a signal when the impedance variation is equal to or greater than a predetermined value. The current source 11 or the voltage measuring unit 12 in the input device 1 is disposed in a circuit section 1A. Various threads can be used as the conductive thread (the electrode thread). For example, a thread in which a metal (a high-conductivity material such as silver or aluminum) is plated with Teflon (registered trademark) can be used as the conductive thread. For example, a conductive material (for example, a carbon material (such as carbon nanotubes or carbon fiber)) or a (yarn-dyed or piece-dyed) thread in which a thread or a cloth is permeated with conductive ink can be applied as the conductor (the conductive thread, the conductive cloth).

Figure 2:
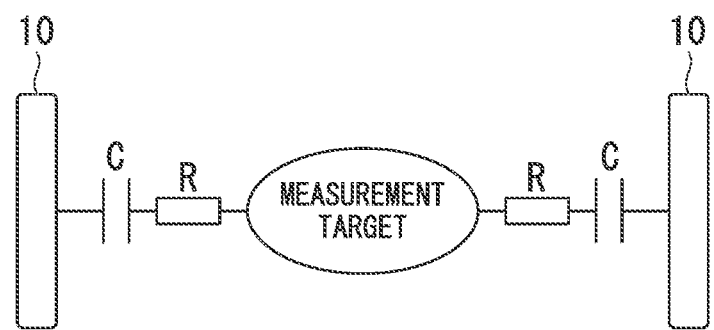
FIG. 2 is a first diagram showing an equivalent circuit of a space between a conductor and a measurement target according to an embodiment of the present invention.

FIG. 2 is a first diagram showing an equivalent circuit of a space between a conductor and a measurement target according to an embodiment of the present invention.

Since a dielectric constant of air is finite, a space (a predetermined area in the vicinity of the conductor, a space in the vicinity of the conductor) can be expressed by the equivalent circuit shown in FIG. 2.

Impedance (|Z|) (of an air layer) between the conductor 10 (electrode) and a measurement target in FIG. 2 can be expressed by Equation (1). Here, frequency is denoted by f, resistance is denoted by R, and capacitance of air is denoted by C.

$$|Z|=\sqrt{R^2+(1/(2\pi f C))^2} \quad (1)$$

Impedance ($|Z_C|$) of a capacitor (C) can be expressed by Equation (2).

$$|Z_c|=1/(2\pi f C) \quad (2)$$

In Equation (2), when a high-frequency current flows, the impedance of the capacitor is a value that becomes infinitely close to 0. When a high-frequency current is input to the conductors 10, a current can flow into air (space) and the measurement target. That is, the input device 1 can determine that a measurement target (for example, a hand) is disposed in the vicinity of the conductors 10 (for example, that an area including at least a part of the conductors 10 is covered with the measurement target) on the basis of the impedance variation even in a state in which the electrodes serving as the conductors 10 and the measurement target are substantially not in contact with each other (or a state in which the measurement target is substantially not in contact with a fiber sheet or an article of clothing) using a high-frequency current. As described above, for example, the conductors 10 constituting the input device 1 are conductive threads. By sewing the conductive threads to a part of an article of clothing (for example, a sleeve, a shoulder, a vicinity of an arm, a collar, a skirt, or a neckline of the article of clothing), the input device 1 can be configured as a unified body with the clothing. For example, when the conductors 10 of the conductive threads are covered with a hand, the input device 1 detects an approach of the hand to the conductive threads on the basis of the impedance variation and outputs a signal. Accordingly, the input device can serve as an input interface. The high-frequency current flowing into the conductors 10 formed of the conductive threads is, for example, a high-frequency current ranging from 100 kHz to 5 MHz. For example, the high-frequency current can be set to about 100 KHz, 150 KHz, 200 KHz, 250 KHz, 300 KHz, 350 KHz, 400 KHz, 450 KHz, 500 KHz, 550 KHz, 600 KHz, 650 KHz, 700 KHz, 750 KHz, 800 KHz, 850 KHz, 900 KHz, 950 KHz, 1 MHz, 1.5 MHz, 2 MHz, 2.5 MHz, 3 MHz, 3.5 MHz, 4 MHz, 4.5 MHz, or 5 MHz or can be set to be in a range acquired in combination of the above-mentioned numerical values. The present invention is not limited to the above-mentioned numerical values. The high-frequency current may be set to be less than 100 KHz or may be set to be equal to or greater than 5 MHz.

Figure 3:
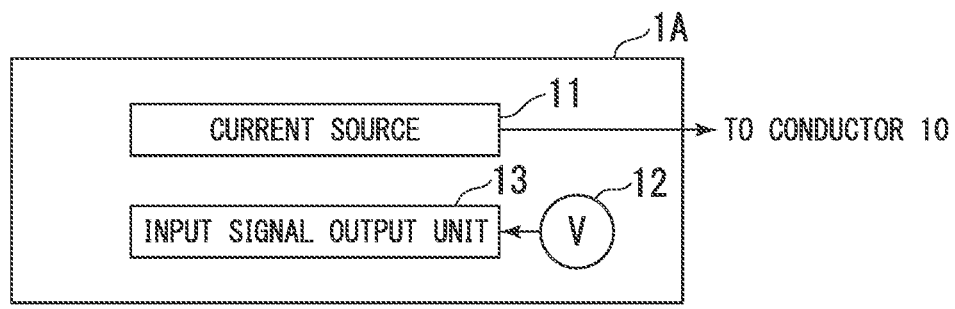
FIG. 3 is a first diagram showing a functional block of a circuit section according to an embodiment of the present invention.

FIG. 3 is a first diagram showing a functional block of circuitry according to an embodiment of the present invention.

The input device 1 includes a circuit section 1A (FIG. 3) that is connected to the conductors 10 shown in FIG. 1. The circuit section 1A includes an input signal output unit 13 in addition to the current source 11 and the voltage measuring unit 12. The input signal output unit 13 is a processor that is configured to output a signal when an impedance variation of the conductors is detected and the variation is significant.

The circuit section shown in FIG. 3 may include a central processing unit (CPU), a memory (a storage unit) such as a read only memory (ROM) or a random access memory (RAM), a battery, and a circuit element such as a capacitor or a resistor. The input signal output unit 13 may be a functional unit that is constituted by causing the CPU to read and execute a program stored in the memory.

Figure 4:
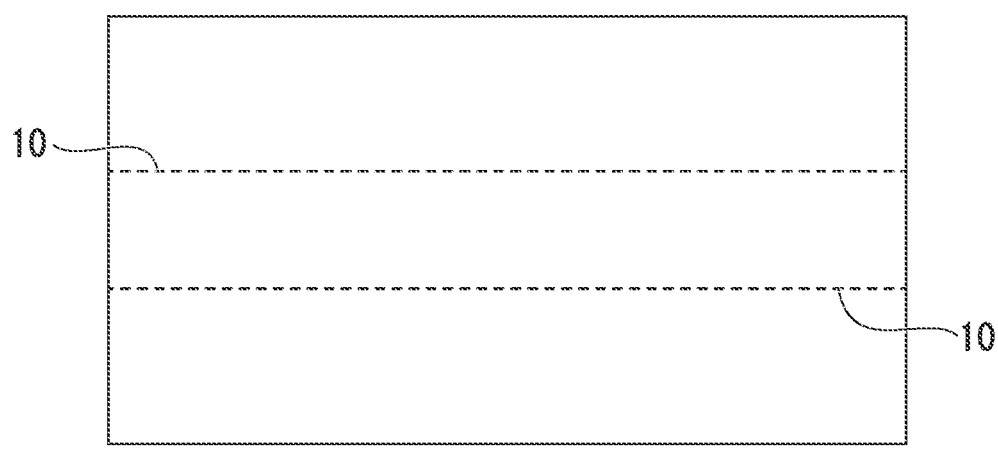
FIG. 4 is a first diagram showing a structure of a fiber sheet to which a conductor is sewn according to an embodiment of the present invention.

FIG. 4 is a first diagram showing a structure of a fiber sheet to which conductors are sewn according to an embodiment of the present invention.

As described above, the conductor 10 according to this embodiment is formed of a conductive thread. The conductive threads are sewn onto a fiber sheet. FIG. 4 shows a piece of a fiber sheet to which a conductive thread is sewn. One or two conductive threads are sewn onto the fiber sheet. FIG. 4 shows a state in which two conductive threads serving as the conductor 10 are sewn onto the fiber sheet. In the embodiment shown in FIG. 4, the conductive threads are sewn straight, but the present invention is not limited to the shape.

Here, the expression "a conductor is sewn onto a fiber sheet (a cloth) (a conductor is set in a fiber sheet (a cloth))" includes, for example, (a) a condition in which the conductor 10 is at least a partial element of a fabric structure of the cloth, (b) a condition in which the conductor 10 is disposed between layers in the cloth having a multi-layered structure (for example, multi-layered fabric structure), (c) a condition in which the conductor 10 is disposed between two layers of the cloth (including a folded part of the cloth) or between the cloth and another material, (d) a condition in which the conductor 10 is disposed as a sewing material in the cloth, (e) a condition in which the conductor 10 is disposed at an end of the cloth, and (f) a condition in which the conductor 10 is disposed in the cloth as a part of a pattern or a design. The conductor 10 can be disposed so as to be observable or substantially non-observable from the outside at the time of usual use. The surface of the conductor 10 may be set to, for example, a color the same as a primary color of cloth, a similar color, or a color different from the primary color of the cloth. The cloth may have at least one of a color, a figure (pattern), characters, and a drawing pattern (design). The cloth is a plate-shaped or a sheet-shaped member formed of a fiber (such as a natural fiber or a synthetic fiber) and includes various kinds. For example, the cloth includes fabric, non-woven fabric, felt, knit, or lace. The cloth has a structure in which warp yarns (warp) and weft yarns (weft) are crossed. In general, the warp yarns are disposed in the length direction of the cloth at the time of weaving and the weft yarns are disposed in the width direction. The repetition of crossing of a predetermined pattern constitutes a fabric structure. In an embodiment, at least a part of the yarns of the cloth may be formed of a conductor. Representative examples of the cloth include synthetic fabric in addition to silk fabric, wool fabric, cotton fabric, and hemp fabric. Various materials can be used as the material of the cloth, and examples thereof include cotton, silk, hemp, mohair, wool, cashmere, and synthetic fiber (such as acetate, cupra, rayon, recycled polyester, nylon, polyurethane, polyester, and Fistop). Examples of the non-woven fabric include a nylon fiber, a polyolefin fiber, a silk fiber, a rayon fiber, a vinylon fiber, a glass fiber, and an aramid fiber. The above-mentioned materials may be used alone or in combination. The cloth and the material thereof are not limited to the above-mentioned examples.

Figure 5:
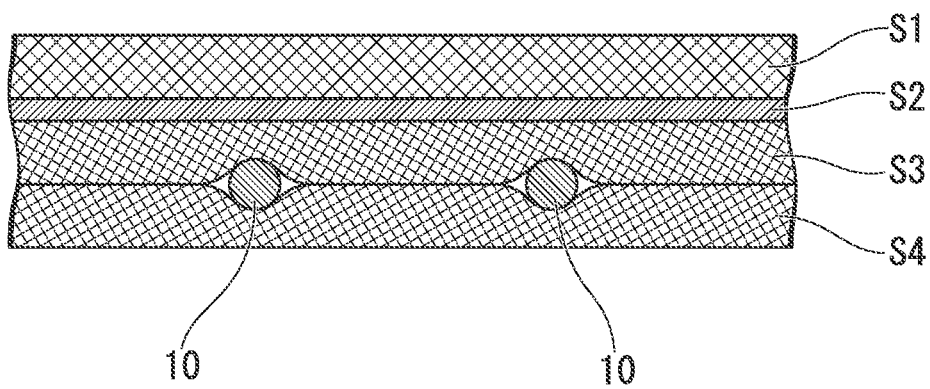
FIG. 5 is a second diagram showing the structure of a fiber sheet to which a conductor is sewn according to an embodiment of the present invention.

FIG. 5 is a second diagram showing a structure of a fiber sheet to which conductors are sewn according to an embodiment of the present invention.

FIG. 5 shows a cross-section of a piece of the fiber sheet shown in FIG. 4. As shown in FIG. 5, the fiber sheet has a configuration in which an insulating layer S1, a shield layer S2, an insulating layer S3, and an insulating layer S4 are stacked from top to bottom. The conductor 10 (the conductive thread) is sewn between the insulating layer S3 and the insulating layer S4. In FIG. 5, two conductors 10 are sewn.

In the shield layer S2, an opening is formed in an input area disposed at a predetermined position of the fiber sheet to constitute the input device 1. That is, in the input device 1, the shield layer S2 is not formed in the structure of the fiber sheet in the input area. When the fiber sheet is used as, for example, a material of clothing, the clothing is manufactured such that the shield layer located in the upper layer is on the outside and the conductor 10 located in the lower layer is on the inside (the side coming in close contact with skin). When a user wearing the clothing covers the vicinity of the input area with a hand in a state in which the input device 1 operates, the input signal output unit 13 of the input device 1 determines an impedance variation via the conductor 10 and outputs a signal. Accordingly, the fiber sheet or the clothing including the input device 1 serves as an input interface.

The structure of the fiber sheet has only to have at least a conductor 10 sewn thereto (a conductor 10 has only to be set in the cloth). In order to provide the fiber sheet with an input area and an area other than the input area, the structure of the fiber sheet has only to include at least an insulating layer to which the conductor 10 is sewn and a shield layer S2 stacked thereon and to have an opening formed in the shield layer S2 in a predetermined area (the input area). For example, in FIG. 5, the insulating layer S3 and the insulating layer S4 may be formed as a unified body, or the insulating layer S2 may not be present. The shield layer S2 may be formed of the same material as the material of the conductor 10, but any material can be used as long as an electrical influence to the conductor 10 from the outside can be intercepted.

It has been described that the conductor 10 has a thin wire shape, but the conductor 10 may have a belt shape. The shape of the conductor 10 is not particularly limited as long as it can determine the impedance variation in the circuit section 1A. The substantial number of layers in the multi-layered fiber sheet may be set to 2, 3, 4, 5, 6, 7, 8, 9, 10, 11, 12, 13, 14, 15, 16, 17, 18, 19, 20, or more. Another object may be attached to the fiber sheet.

Figure 6:
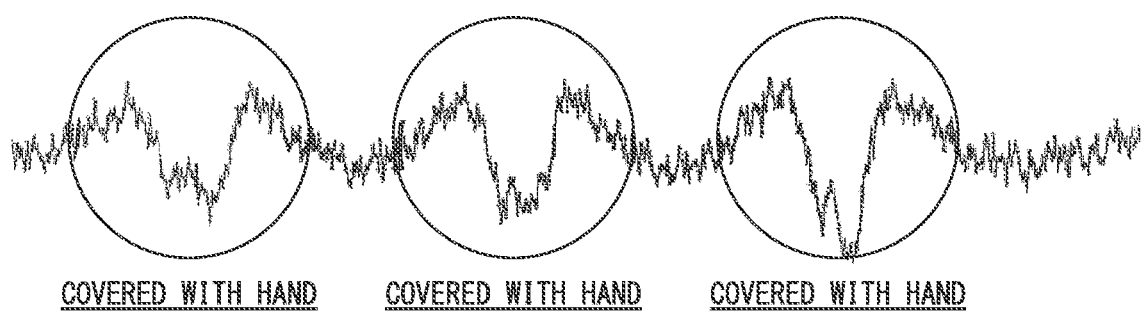
FIG. 6 is a diagram showing an impedance variation according to an embodiment of the present invention.

FIG. 6 is a diagram showing an impedance variation according to an embodiment of the present invention.

The input signal output unit 13 detects the impedance variation shown in FIG. 6. When the vicinity of the conductor 10 (an electric field area) in the input area is covered with a measurement target such as a hand in a state in which the current source 11 of the input device 1 inputs a high-frequency current to the conductor 10 as described above, the voltage value measured by the voltage measuring unit 12 varies when the hand is put in the electric field area. The input signal output unit 13 detects the impedance variation shown in FIG. 6.

In the configuration of the input device 1 shown in FIG. 1, the impedance value decreases when covering with the hand is performed.

The vertical axis in FIG. 6 represents increasing impedance values from the bottom to the top.

The input device 1 can be assumed to be attached to clothing or a fiber sheet. For example, an input area can be set to an area in a sleeve of an article of clothing. For example, the circuit section 1A can be built in a pouch, a pocket, or a patch, or the like attached to the clothing. The conductor 10 (an extending portion electrically connecting the conductor 10 and the circuit section 1A) which is drawn out from the circuit section 1A to the input area is shielded by the shield layer S2 as shown in FIG. 5. The input signal output unit 13 of the circuit section 1A outputs a signal on the basis of detection of the impedance variation and outputs, for example, an ON signal for turning on a certain electrical device. Alternatively, the input signal output unit 13 may alternately output an ON signal and an OFF signal on the basis of the impedance variation. The input signal output unit 13 may correct a value in a state in which impedance is stable (stable state) when the input area is not covered with a measurement target such as a hand to 0 and may output the signals when the impedance variation from the value is equal to or greater than a predetermined threshold value. The input signal output unit 13 may output a signal based on a pattern of the detected impedance variation of the conductor 10. For example, the input signal output unit 13 determines the number of times the impedance variation becomes equal to or greater than the threshold value in a predetermined period. When the number of times reaches a predetermined value, the input signal output unit may output a drive signal or a control signal for driving another electrical device electrically connected to the circuit section 1A.

For example, the circuit section 1A may include a wireless communication circuit and may transmit the signal output from the input signal output unit 13 to another external electrical device or the like. For example, the input signal output unit 13 may output a television control signal for turning on a power supply of a television or changing a channel. In this case, the wireless communication circuit of the circuit section 1A may transmit the television control signal to the television and the television may receive the television control signal and change the channel of the television or perform control of turning on or off the power supply. The input signal output unit 13 includes a memory and stores control information for each electrical device in the memory. The input signal output unit 13 may read the control information of the electrical device based on the pattern of the detected impedance variation of the conductor 10 (the number of times or the timing at which the impedance value per unit time becomes greater than the threshold value, etc.) and may transmit the control information via the wireless communication circuit. The circuit section 1A may include a wired communication circuit instead of the wireless communication circuit, which is connected to an electrical device via a communication cable.

Figure 7:
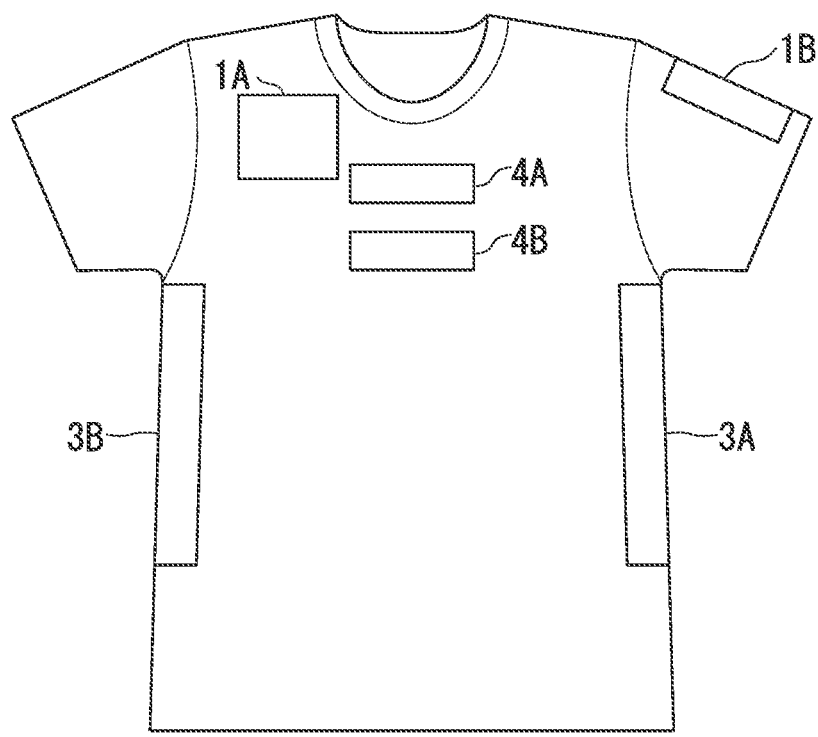
FIG. 7 is a diagram showing an article of clothing according to an embodiment of the present invention.

FIG. 7 is a diagram showing clothing according to an embodiment of the present invention.

In FIG. 7, reference numeral 1A denotes a circuit section of an input device. Reference numeral 1B denotes an input area. Although not shown in FIG. 7, the conductor 10 (a first conductor) connected to the circuit section 1A extends to the input area 1B. A portion of the conductor 10 (an extending portion) extending from the circuit section 1A, that is, a portion (a fiber sheet) to which the conductor 10 is sewn in an area other than the input area 1B, is provided with the shield layer S2 shown in FIG. 5. The shield layer S2 can cover the extending portion to electrically shield the extending portion. According to this configuration, even when a portion other than the input area 1B of the conductor 10 extending from the circuit section 1A is covered with a measurement target such as a hand, the impedance variation thereof is not detected and it is thus possible to prevent an erroneous operation of the input device. The conductor 10 extending from the circuit section 1A to the input area 1B is configured to include two conductors as shown in FIG. 1. A plurality of sets of two conductors 10 which are connected to the circuit section 1A and which extend from the circuit section 1A to the input area 1B may be provided. In this case, the sets of two conductors 10 extend to different areas in the input area 1B. In the sets of conductors 10 extending to different areas in the input area 1B, the shield layer S2 is stacked in an area other than the extending area. According to this configuration, the input device 1 can detect whether any one of the different areas in the input area 1B is covered with a hand. Accordingly, the input device 1 can output a signal corresponding to the area in the input area 1B when the impedance variation is detected.

The clothing shown in FIG. 7 is provided with a fabric electrode area constituted by a fiber sheet to which the conductor 10 is sewn. In FIG. 7, reference numerals 3A and 3B denote a set of first fabric electrode areas (first belt-shaped electrodes) as a combination thereof. In FIG. 7, reference numerals 4A and 4B denote a set of second fabric electrode areas (second belt-shaped electrodes) as a combination thereof. Each of the fabric electrode areas (3A, 3B, 4A, and 4B) has a configuration in which one (one electrode) of the set of (two) conductors 10 (second conductors) shown in FIG. 1 is sewn onto the fiber sheet. That is, the set of fabric electrode areas 3A and 3B (or 4A and 4B) has a configuration equivalent to that of the fiber sheet (in which two conductors 10 are separated from each other) shown in FIG. 1. A biological information detection device 100 is constituted by one set of fabric electrode areas (a combination of 3A and 3B or a combination of 4A and 4B) and the circuit section 1A. The conductors 10 which are drawn from the circuit section 1A to the fabric electrode areas 3A, 3B, 4A, and 4B are shielded with the shield layer S2 as shown in FIG. 5. In this case, the shield layer S2 may be disposed on the outer side of the clothing with respect to the conductors 10 which are drawn, or may be disposed on the inner side of the clothing with respect to the conductors 10. The shield layer 2 may be disposed on both the inner side and the outer side of the conductors 10 which are drawn. In the fabric electrode areas 3A, 3B, 4A, and 4B, the shield layer 2 may be disposed on the outer side of the clothing with respect to the conductors 10 or may not be disposed.

The input device 1 and the biological information detection device 100 are equivalent to each other in configuration, but are different from each other in whether a processing unit that outputs an input signal on the basis of the impedance variation or a processing unit configured to determine biological information is provided as a processing unit. In this embodiment, the fabric electrode areas 3A and 3B are attached to both armpits (positions of an article of clothing corresponding to the positions of the lungs) of a shirt with the lungs to be measured interposed therebetween. In this embodiment, the fabric electrode areas 4A and 4B are attached to the vicinity of the heart (positions of the article of clothing corresponding to the position of the heart) to be measured. When the biological information detection device 100 inputs a high-frequency current to the combination of the fabric electrode areas 3A and 3B, the current passes through a living body (in the vicinity of the lungs) between the fabric electrode areas 3A and 3B and an electric field is generated in the living body. When the biological information detection device 100 inputs a high-frequency current to the combination of the fabric electrode areas 4A and 4B, the current flows radially through a living body (in the vicinity of the heart) between the fabric electrode areas 4A and 4B and a radial electric field is generated in the living body.

Figure 8:
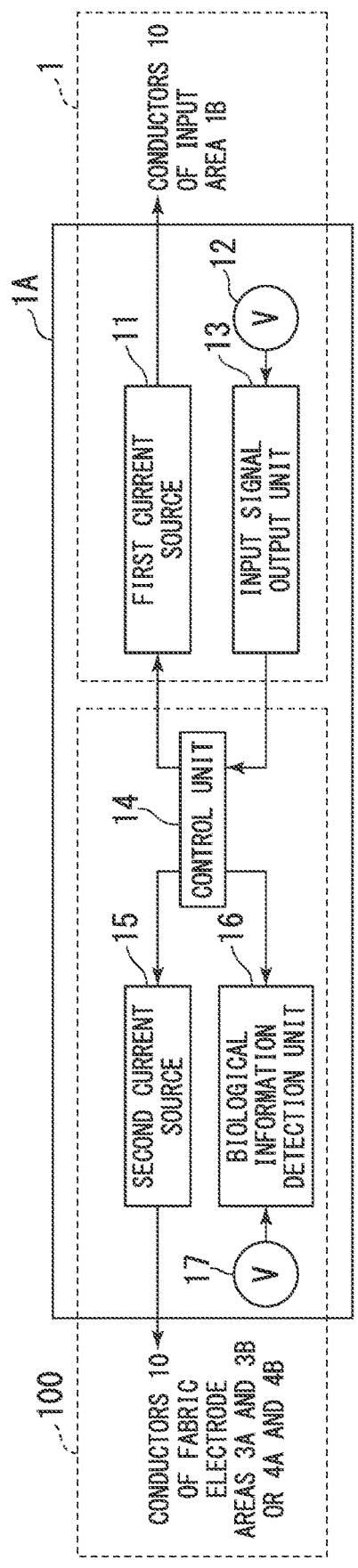
FIG. 8 is a second diagram showing a functional block of a circuit section according to an embodiment of the present invention.

FIG. 8 is a second diagram showing functional blocks of the circuit section according to an embodiment of the present invention.

When the fabric electrode areas shown in FIG. 7 are provided in an article of clothing or the like, the circuit section 1A includes a control unit 14, a second current source 15 (a second current input source, a second input source), a biological information detection unit 16, and a voltage measuring unit 17 (a second voltage measuring unit) in addition to the current source 11, the voltage measuring unit 12 (the first voltage measuring unit), and the input signal output unit 13 which are shown in FIG. 3.

The control unit 14 performs a process of controlling the functional units (the first current source 11, the input signal output unit 13, the second current source 15, and the biological information detection unit 16) of the circuit section 1A.

The second current source 15 inputs a high-frequency current (a second high-frequency current) to the conductors 10 of the fabric electrode areas 3A, 3B, 4A, and 4B.

The biological information detection unit 16 determines a pulmonary ventilation rate (biological information) based on the impedance variation acquired from the fabric electrode areas 3A and 3B on the basis of the biological information detection start signal acquired from the input signal output unit 13 via the control unit 14. Alternatively, the biological information detection unit 16 determines heartbeat information (biological information) based on the impedance variation acquired from the fabric electrode areas 4A and 4B on the basis of the biological information detection start signal acquired from the input signal output unit 13 via the control unit 14. The biological information detection unit 16 may switch its operation between detection of the pulmonary ventilation rate and detection of the heartbeat information on the basis of the biological information detection start signal acquired from the input signal output unit 13 via the control unit 14.

The circuit section 1A shown in FIG. 8 includes a central processing unit (CPU), a storage unit such as a read only memory (ROM) or a random access memory (RAM), a battery, and a circuit element such as a capacitor or a resistor. The input signal output unit 13, the control unit 14, and the biological information detection unit 16 may be functional units which are constituted by causing the CPU to read and execute a program.

Figure 9:
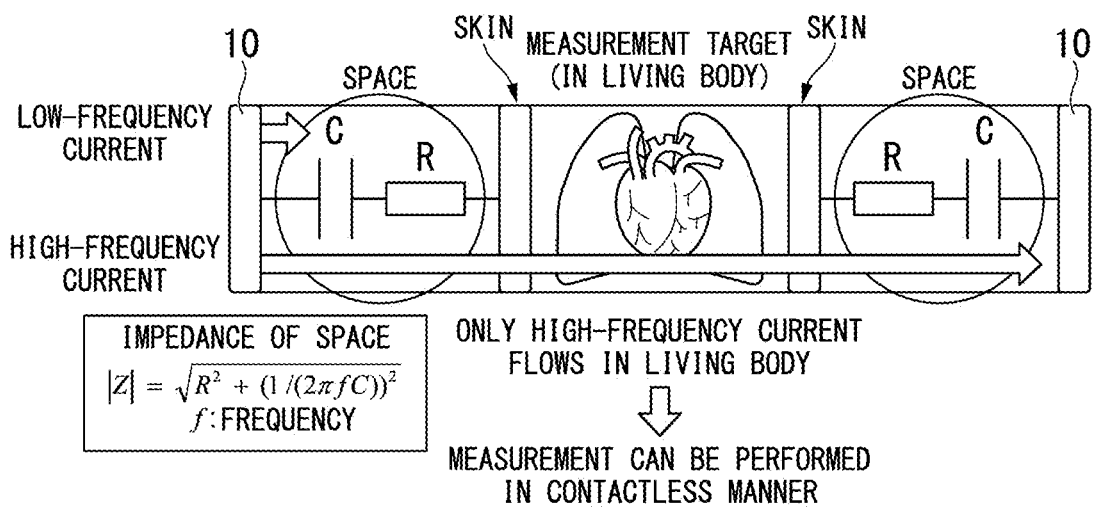
FIG. 9 is a second diagram showing an equivalent circuit of a space between a conductor and a measurement target according to an embodiment of the present invention.

FIG. 9 is a second diagram showing an equivalent circuit of a space between a conductor and a measurement target according to an embodiment of the present invention.

This equivalent circuit is equivalent to the equivalent circuit shown in FIG. 2. The biological information detection device 100 including the fabric electrode areas 3A and 3B and the circuit section 1A shown in FIG. 7 measures the lungs of a living body. When the second current source 15 of the circuit section 1A inputs a high-frequency current to the conductors 10 sewn onto fiber sheets of the fabric electrode areas 3A and 3B under the control of the control unit 14, the high-frequency current flows in the living body. The high-frequency current flowing into the conductors 10 formed of conductive threads is a current ranging, for example, from 100 KHz to 5 MHz in the biological information detection device 100. When the current flowing in the conductor 10 is a low-frequency current, the current cannot flow in the living body. The frequency of the high-frequency current input to the conductor 10 by the biological information detection device 100 and the frequency of the high-frequency current input to the conductor 10 by the input device 1 may be equal to or different from each other. The frequency of the high-frequency current input to the conductors sewn onto the combination of the fabric electrode areas 3A and 3B by the biological information detection device 100 and the frequency of the high-frequency current input to the conductors 10 sewn onto the combination of the fabric electrode areas 4A and 4B may be equal to or different from each other. The frequency of the high-frequency current input to the conductors 10 by the biological information detection device 100 or the input device 1 is a frequency with which a variation in the impedance value can be detected due to presence or variation (a variation in an amount of air or an amount of blood due to expansion of the lungs or the heart) of a measurement target (such as a hand or an organ in a living body).

Here, respiration is a series of operations of inhaling air from the atmosphere into the lungs and exhaling air from the lungs to the atmosphere. The fabric electrode areas 3A and 3B are attached to positions of an article of clothing corresponding to the positions of the lungs and the second current source 15 causes a high-frequency current to flow through the conductors 10 of the fabric electrode areas 3A and 3B. Accordingly, the biological information detection unit 16 can detect an impedance variation which is generated due to inhalation and exhalation to and from the lungs caused by the respiration in the same principle as described above with reference to the input device 1. More specifically, since impedance of air is high, the impedance value of the lungs decreases as the amount of air flowing into the lungs decreases (which corresponds to an amount of air exhaled). Accordingly, when the lungs expand, the amount of air increases (which corresponds to an amount of air inhaled) and thus the biological information detection unit 16 determines the increase of the impedance value. On the other hand, when the lungs contract and air flows out of the lungs, the biological information detection unit 16 determines variation in which the impedance decreases.

In this way, the amount of air ventilated in the lungs can be determined by the biological information detection device 100 including the fabric electrode areas 3A and 3B and the circuit section 1A. The fabric electrode areas 3A and 3B are formed of a fiber sheet to which conductive threads are sewn. Accordingly, since the amount of air ventilated in the lungs can be measured merely by disposing the fiber sheet in the vicinity of the lungs, it is not necessary to bring electrodes into close contact with skin in the vicinity of the lungs. Even when a user serving as a measurement target wears clothes, the amount of air ventilated in the lungs can be determined in a contactless manner by wearing the clothing shown in FIG. 7 thereover. That is, it is possible to determine an amount of air ventilated in the lungs in a contactless manner. Accordingly, it is possible to reduce a burden or discomfort (constraint) due to fastening of a user serving as a measurement target at the time of measurement of the pulmonary ventilation rate. Particularly, in the case of a symptom such as apnea, it is necessary to measure an amount of air ventilated by the user serving as a measurement target at night, and measurement using a flowmeter with a mask, measurement by a nasal pressure sensor or detection of a decrease in chest girth, or the like has been required conventionally. That is, the conventional ventilation rate measuring techniques have required a mechanism coming in close contact with a user's body. On the other hand, according to the biological information detection device 100, it is possible to measure an amount of air ventilated in the lungs in a contactless manner and thus to reduce a burden on a user serving as a measurement target.

According to the biological information detection device 100, since an increase or a decrease in the amount of air flowing into the lungs is directly detected on the basis of the impedance variation, it is possible to determine the amount of air ventilated with certain accuracy even in a contactless manner.

The technique of measuring a measurement target on the basis of the impedance variation in a contactless manner is hereinafter referred to as contactless impedance measurement.

Figure 10:
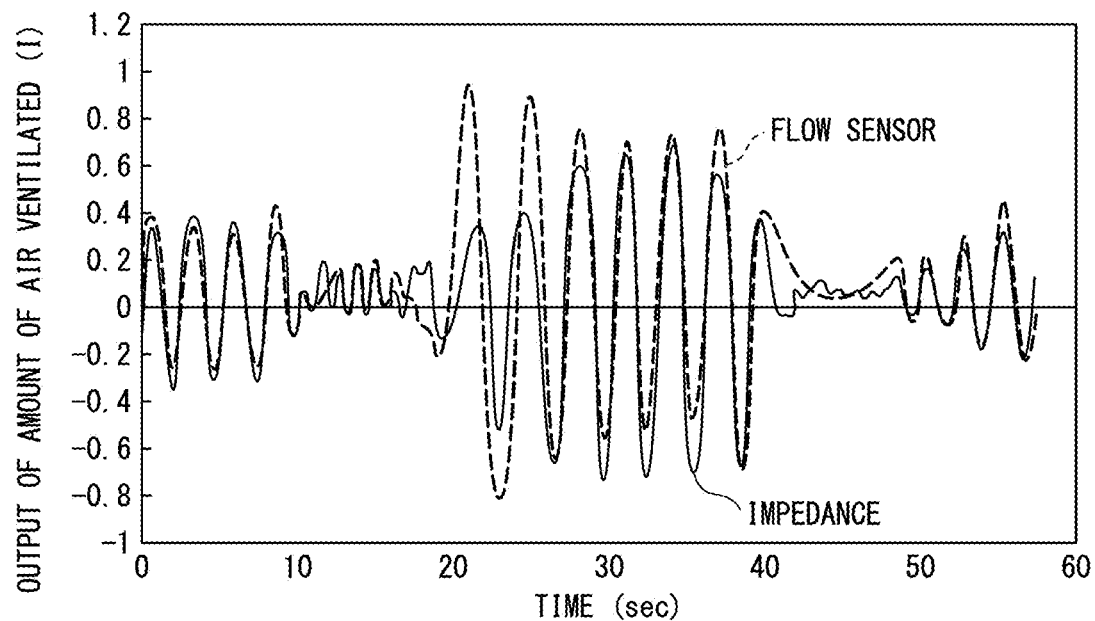
FIG. 10 is a diagram showing a ventilation rate measurement graph based on contactless impedance measurement according to an embodiment of the present invention.

FIG. 10 is a diagram showing a ventilation rate measurement graph based on the contactless impedance measurement according to an embodiment of the present invention.

In FIG. 10, the ventilation rate measured by the contactless impedance measurement is indicated by a solid line (which is described as impedance in FIG. 10). The vertical axis of the drawing represents the ventilation rate. In FIG. 10, an actual ventilation rate measured by a flow sensor is indicated by a dotted line. The flow sensor is a sensor that physically measures an amount of air flowing from a mouth-nose mask. The horizontal axis of the drawing represents the time. According to the drawing, a very small amount of ventilated air of about 200 cc (0.2 liter) which is difficult to imagine in general is detected between 10 seconds and 20 seconds after the measurement is started (0 seconds). Since this very small amount of ventilated air can be detected, the biological information detection device 100 can accurately determine a sleep respiration disorder (apnea). Between 20 seconds and 40 seconds after the measurement is started, there is a difference between the measurement of impedance and the measurement of the amount of air ventilated using the flow sensor, but this is based on a time delay of a smoothing filer due to a rapid increase of the amount of air ventilated. When 40 seconds elapses after the measurement is started, it can be seen that the timings at which the waveforms in the results of the measurement of impedance and the measurement using the flow sensor increase or decrease or the timings of peaks substantially agree with each other and the amount of air ventilated can be accurately detected.

The biological information detection unit 16 can measure an amount of air ventilated better so as to be equivalent to the value measured by the flow sensor in FIG. 10 by multiplying the detected impedance value by a proper correction coefficient. Here, the biological information detection unit 16 may determine a posture of a user wearing an article of clothing having the biological information detection device 100 attached thereto, for example, using a posture detection device (such as a gyroscope) separately disposed in the biological information detection device 100 and may correct the detected impedance value using a correction coefficient based on the detected posture. For example, a posture detecting circuit detects any one of a sitting position (upright), a supine position, and a lateral decubitus and the biological information detection unit 16 acquires the detection result. Then, the biological information detection unit 16 reads a correction coefficient from a memory on the basis of the detection result of the posture detecting circuit indicating any one of a sitting position (upright), a supine position, and a lateral decubitus. Then, the biological information detection unit 16 calculates an amount of air ventilated on the basis of the detected impedance value and the read correction coefficient.

The biological information detection device 100 including the fabric electrode areas 4A and 4B and the circuit section 1A shown in FIG. 7 measures the heart of a living body. When the second current source 15 of the circuit section 1A outputs a high-frequency current to the conductors 10 sewn onto the fiber sheets of the fabric electrode areas 4A and 4B under the control of the control unit 14, the high-frequency current flows in the living body.

An amount of blood in the heart varies depending on heartbeats. The fabric electrode areas 4A and 4B are attached to positions of an article of clothing corresponding to the position of the heart and the second current source 15 causes a high-frequency current to flow in the conductors 10 of the fabric electrode areas 4A and 4B. Accordingly, the biological information detection unit 16 can determine an impedance variation caused by an increase or a decrease in the amount of blood in the heart based on the heartbeats in the same principle as described above in the input device 1. More specifically, since the impedance of blood is low, the impedance of the heart increases as the amount of blood in the heart decreases. Accordingly, when the heart contracts, the biological information detection unit 16 determines that the impedance varies to increase. On the other hand, when the heart expands and blood flows into the heart, the biological information detection unit 16 determines that the impedance varies decreasingly.

In this way, measurement of heartbeat information of the heart can be performed by the biological information detection device 100 including the fabric electrode areas 4A and 4B and the circuit section 1A. The fabric electrode areas 4A and 4B are formed of a fiber sheet to which a conductive thread is sewn. Accordingly, since the heartbeat information of the heart can be measured by only disposing the fiber sheet in the vicinity of the heart, it is not necessary to bring electrodes into close contact with a skin. Even when a user as a measurement target wears clothes, the heartbeat information can be measured in a contactless manner by wearing the clothing shown in FIG. 7 thereon. That is, it is possible to determine heartbeat information in a contactless manner. Accordingly, it is possible to reduce burden or discomfort (constraint) due to fastening of a user as a measurement target at the time of measurement of the heartbeat information.

According to the biological information detection device 100, since an increase or a decrease in an amount of blood in the heart is directly detected on the basis of an impedance variation, it is possible to determine heartbeat information with higher accuracy than that in the related art. The biological information detection device 100 determines the number of heartbeats per unit time, for example, on the basis of the number of peaks per unit time based on the impedance variation.

Figure 11:
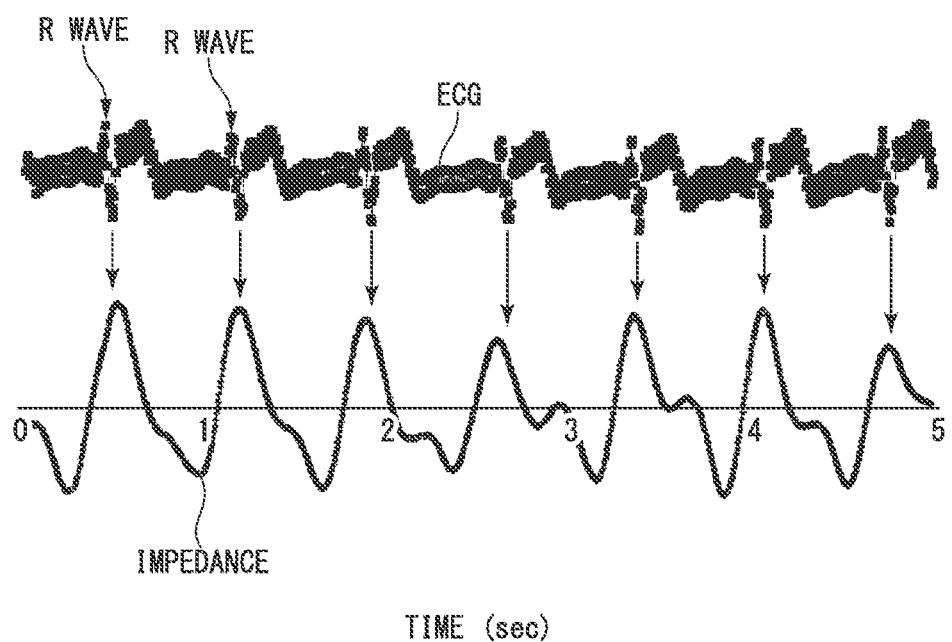
FIG. 11 is a diagram showing a heartbeat information measurement graph based on contactless impedance measurement according to an embodiment of the present invention.

FIG. 11 is a diagram showing a heartbeat information measurement graph based on contactless impedance measurement according to an embodiment of the present invention.

In FIG. 11, a heartbeat waveform measured by the contactless impedance measurement is indicated by a solid line on the lower side of the graph (which is described as impedance in FIG. 11). An electrocardiographic waveform actually measured by an electrocardiograph (ECG) is shown on the upper side of the graph. The horizontal axis represents the time. According to this drawing, it can be seen that timings at which an R wave appear in the electrocardiograph (timings at which the heart contracts) substantially agree with timings of peaks of the impedance waveform.

Figure 12:
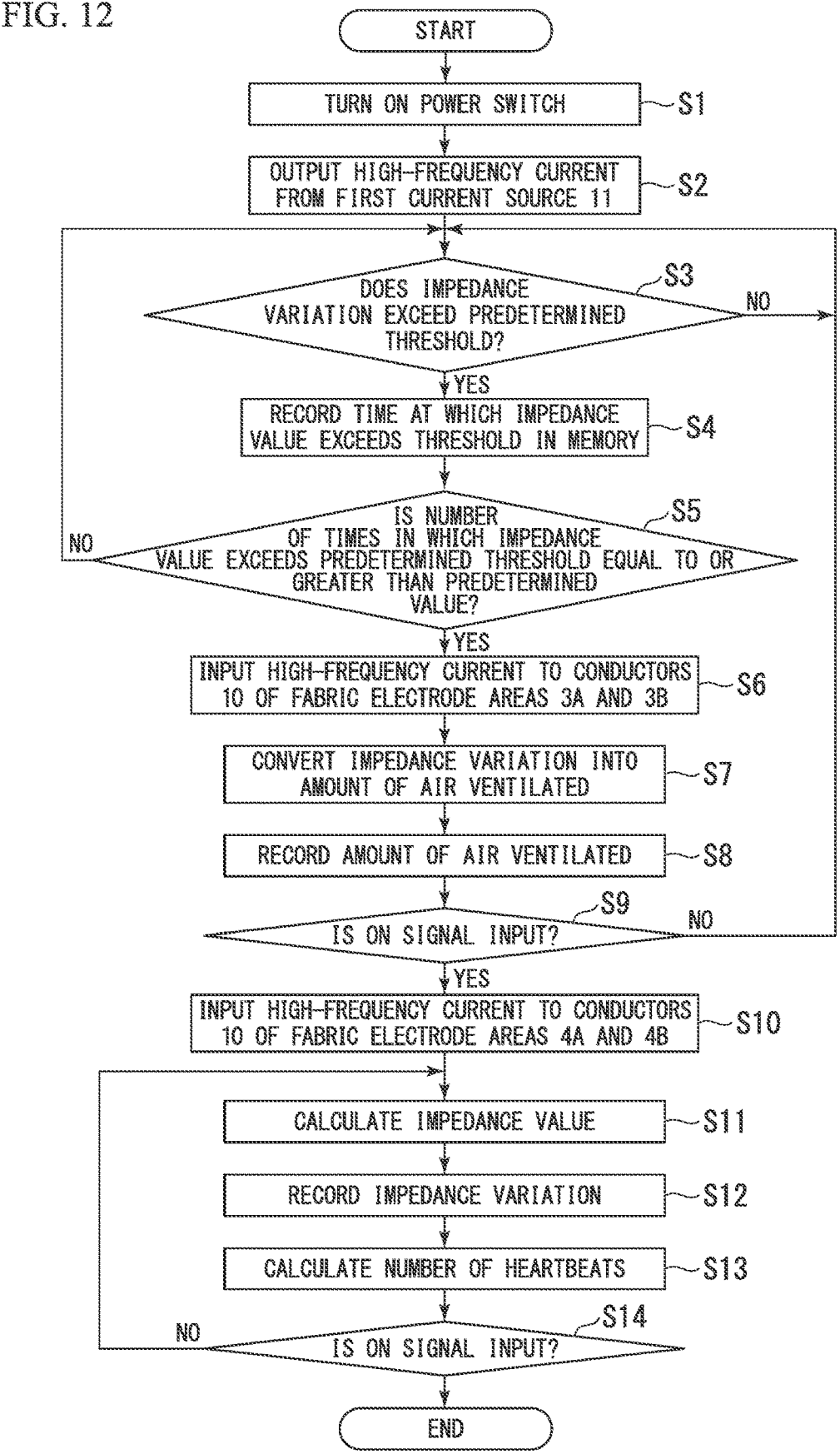
FIG. 12 is a diagram showing a process flow in a circuit section according to the embodiment.

FIG. 12 is a diagram showing a process flow in the circuit section according to the embodiment.

A process flow in the circuit section will be described below with reference to FIG. 12.

First, a power switch of the circuit section 1A is turned on by an operation of a user wearing the clothing shown in FIG. 7 (Step S1). Then, the control unit 14 instructs the first current source 11 to output a current to the conductors 10 of the input device 1. Then, the first current source 11 outputs a high-frequency current (Step S2). In this state, the user covers the input area with a hand. The input signal output unit 13 calculates the impedance value on the basis of a voltage measurement result of the voltage measuring unit 12. The input signal output unit 13 determines a variation from the impedance value in a stable state. Specifically, the input signal output unit 13 determines whether the variation in the impedance value in the stable state exceeds a predetermined threshold value (Step S3). When the variation in the impedance value in the stable state exceeds the predetermined threshold value, the input signal output unit 13 records the time in the memory (Step S4). When the input area is covered with a hand, the input signal output unit 13 determines the variation in the impedance value and sequentially records the time when the variation in the impedance value exceeds the predetermined threshold value in the memory. On the basis of the times recorded in the memory, the input signal output unit 13 determines the number of times in which the variation in the impedance value exceeds the predetermined threshold value during a unit time (per unit time) based on the first time when the variation in the impedance value exceeds the predetermined threshold value. The input signal output unit 13 determines whether the number of times in which the variation in the impedance value per unit time exceeds the predetermined value is equal to or greater than a predetermined value (three) (Step S5). For example, when the number of times in which the variation in the impedance value per unit time exceeds the predetermined value is equal to or greater than three, the input signal output unit 13 outputs an ON signal to the control unit 14.

When the ON signal is input from the input signal output unit 13, the control unit 14 outputs a biological information detection start signal to the second current source 15 and the biological information detection unit 16. When the biological information detection start signal is acquired from the control unit 14, the second current source 15 inputs a high-frequency current to the conductors 10 of the fabric electrode areas 3A and 3B (Step S6). When the biological information detection start signal is first input from the control unit 14, the biological information detection unit 16 starts measurement of an amount of air ventilated. The voltage measuring unit 17 measures a voltage and outputs the measured voltage to the biological information detection unit 16. The biological information detection unit 16 calculates the impedance value on the basis of the voltage measurement result of the voltage measuring unit 17. Then, the biological information detection unit 16 determines a variation from the impedance value in the stable state. The biological information detection unit 16 converts the impedance variation into an amount of air ventilated on the basis of the impedance variation and a correction equation, a correction table, or the like (Step S7). The biological information detection unit 16 repeatedly calculates the amount of air ventilated at short time intervals (for example, intervals of several milliseconds). Then, the biological information detection unit 16 records the amount of air ventilated at each time in the memory with the lapse of time.

Through the above-mentioned processes, the information of the amount of air ventilated at each time with the lapse of time is accumulated in the memory. When the biological information detection device 100 includes an output unit such as a liquid crystal screen, the biological information detection unit 16 may output information of a waveform based on the amount of air ventilated to the output unit. Alternatively, the biological information detection unit 16 may transmit the information of the amount of air ventilated to an external monitor device via the wireless communication circuit.

While the above-mentioned processes are performed, the control unit 14 determines whether an ON signal is input from the input device 1 (Step S9). Here, it is assumed that a user covers the input area of the input device 1 with a hand three times. Then, the input signal output unit 13 outputs a second ON signal to the control unit 14. When the ON signal is input from the input signal output unit 13 (YES in Step S9), the control unit 14 outputs a second biological information detection start signal to the second current source 15 and the biological information detection unit 16. When the second biological information detection start signal is input from the control unit 14, the second current source 15 stops outputting a high-frequency current to the conductors 10 of the fabric electrode areas 3A and 3B and inputs a high-frequency current to the conductors 10 of the fabric electrode areas 4A and 4B (Step S10). When the second biological information detection start signal is input from the control unit 14, the biological information detection unit 16 switches measurement of the pulmonary ventilation rate to measurement of the heartbeat information. The voltage measuring unit 17 measures a voltage and outputs the measured voltage to the biological information detection unit 16. The biological information detection unit 16 calculates the impedance value on the basis of the voltage measurement result of the voltage measuring unit 17 (Step S11). The biological information detection unit 16 repeatedly calculates the impedance value at short time intervals (for example, intervals of several milliseconds). The biological information detection unit 16 records the impedance variation at each time in the memory with the lapse of time (Step S12). The biological information detection unit 16 calculates the number of heartbeats per unit time on the basis of the number of peaks per unit time based on the impedance variation (Step S13) and records the calculated number of heartbeats in the memory. Through the above-mentioned processes, the heartbeat information at each time with the lapse of time is accumulated in the memory. When the biological information detection device 100 includes an output unit such as a liquid crystal screen, the biological information detection unit 16 may output information of the number of heartbeats to the output unit. Alternatively, the biological information detection unit 16 may transmit the information of the number of heartbeats to an external monitor device via the wireless communication circuit.

The control unit 14 determines whether an ON signal is input again (Step S14) and stops the process flow when a third ON signal is input.

The measurement of a pulmonary ventilation rate is switched to the measurement of heartbeat information on the basis of the input of the ON signal in the above-mentioned processes, but after the determination result of Step S5 is YES, measurement and recording of the amount of air ventilated in Steps S6 to S8 and measurement and recording of the number of heartbeats in Steps S11 to S13 may be simultaneously performed (the measurements are simultaneously performed by sequentially switching the two measurements at a high speed). Accordingly, it is possible to measure a pulmonary ventilation rate and the number of heartbeats in sleep.

The clothing shown in FIG. 7 includes the combination of fabric electrode areas 3A and 3B and the combination of fabric electrode areas 4A and 4B, but may include only one combination. The biological information detection device 100 may be configured to determine only one of the pulmonary ventilation rate and the heartbeat information. The biological information detection device 100 may determine biological information (for example, a fat volume based on impedance) other than the pulmonary ventilation rate and the heartbeat information.

While the measurement target has been described to be a living body such as a hand, lungs, or an organ, the measurement target is not particularly limited as long as an impedance variation can be detected by inputting a predetermined high-frequency current.

The above-mentioned input device 1 or biological information detection device 100 has a computer system therein. The above-mentioned process steps are stored in a computer-readable recording medium in the form of a program and the process steps are performed by causing a computer to read and execute the program.

The program may be configured to realize a part of the above-mentioned functions. The program may be a program, that is, a so-called differential file (differential program), capable of realizing the above-mentioned functions in combination with a program recorded in advance in a computer system.

DESCRIPTION OF THE REFERENCE SYMBOLS

1 Input device
1A Circuit section
1B Input area
3A, 3B Fabric electrode area (first fabric electrode area, first belt-shaped electrode)
4A, 4B Fabric electrode area (second fabric electrode area, second belt-shaped electrode)
10 Conductor (electrode thread)
11 Current source (first current source, first input source)
12 Voltage measuring unit
13 Input signal output unit
14 Control unit
15 Second current source (second input source)
16 Biological information detection unit
17 Voltage measuring unit
100 Biological information detection device

The invention claimed is:

1. An article of clothing comprising:
   a textile cloth with a measurement region, the textile cloth being located inside and outside of the measurement region;
   circuitry attached to the textile cloth and configured to generate a high-frequency current in a range from 100 kHz to 5 MHz;
   at least two conductors that are set in the cloth and extend from the circuitry into the measurement region so as to not be in direct contact with a skin of a measurement target, the at least two conductors terminating inside the measurement region and being configured to convey the high-frequency current to the measurement region; and
   a shield set in the textile cloth and positioned to cover the at least two conductors between the circuitry and the measurement region so that the at least two conductors remain uncovered by the shield in the measurement region,
   wherein the circuitry is configured to determine an impedance variation within the measurement region based on a voltage value between the at least two conductors, which are electrically separated from each other at the measurement region,
   wherein the measurement region of the textile cloth includes only the textile cloth and the at least two conductors so that the portions of the at least two conductors inside the measurement region form an electrode that is integrated with the textile cloth and transmits the high-frequency current into the measurement target in a contactless manner.

2. The article of clothing according to claim 1, wherein the at least two conductors are set in the textile cloth to satisfy at least one of (a) a first condition that at least a part of one of the at least two conductors be at least a partial element of a fabric structure of the textile cloth, (b) a second condition that at least a part of one of said at least two conductors be disposed between layers in the textile cloth having a multi-layered structure, (c) a third condition that at least a part of one of said at least two conductors be disposed between two layers of the textile cloth, (d) a fourth condition that at least a part of one of said at least two conductors be disposed as a sewing material in the textile cloth, (e) a fifth condition that at least a part of one of said at least two conductors be disposed at an end of the textile cloth, and (f) a sixth condition that at least a part of one of said at least two conductors be disposed in the textile cloth as a part of a pattern or a design.

3. The article of clothing according to claim 1, wherein the at least two conductors include a first pair of conductors which are integrated into the textile cloth and terminate at positions corresponding to lungs and a second pair of conductors which are integrated into the textile cloth and terminate at positions corresponding to a heart,
   wherein the article of clothing further comprises a biological information detection unit configured to determine a pulmonary ventilation rate and/or heartbeat information based on a signal from the circuitry.

4. The article of clothing according to claim 3, wherein the circuitry is configured to output a biological information detection start signal for driving the biological information detection unit depending on a pattern of the determined impedance variation.

5. The article of clothing according to claim 1, wherein the at least two conductors have a thread shape or a belt shape.

6. The article of clothing according to claim 1, wherein the circuitry comprises an input source configured to apply the high-frequency current to the at least two conductors.

7. A biological information detection device comprising:
   a first pair of conductors that are set in an article of clothing so as not to be in direct contact with a skin of a living body;
   a second pair of conductors that are set in the article of clothing and terminate at positions corresponding to lungs and/or a heart in the living body so as not to be in direct contact with the skin of the living body;
   circuitry that is connected to the first pair of conductors and the second pair of conductors and is configured to determine an impedance variation in an area in a vicinity of the termination points of the first pair of conductors based on a voltage value between the first pair of conductors, which are electrically separated from each other at the area, the circuitry being further configured to apply a first high-frequency current in a range from 100 kHz to 5 MHz to the first pair of conductors; and
   a biological information detection unit configured to determine biological information based on a second voltage value between the second pair of conductors, which are electrically separated from each other, the circuitry being further configured to apply a second high-frequency current in a range from 100 kHz to 5

MHz to the second pair of conductors so that the second high-frequency current flows into the living body at a target area in a contactless manner, the termination points of the second pair of conductors being located in the target area; and a shield that covers a part of the second pair of conductors located outside of the target area so that the portions of the second pair of conductors inside the target area remain uncovered by the shield, wherein the target area includes only a textile cloth and the second pair of conductors, the textile cloth being located inside and outside the target area.

8. A biological information detection device comprising:

two conductors that are set in a textile cloth so as not to be in direct contact with a skin of a living body, the two conductors terminating in a target area of the textile cloth;

circuitry that is connected to the two conductors and is configured to determine biological information based on a voltage value between the two conductors, which are electrically separated from each other at the target area; and a shield that covers portions of the two conductors that are outside of the target area so that the two conductors remain uncovered by the shield in the target area, wherein the shield is configured to be between the covered portions of the two conductors and the living body, wherein the circuitry is configured to apply a high-frequency current in a range from 100 kHz to 5 MHz to the target area so that the high-frequency current flows in the living body in a contactless manner between the two conductors and the skin of the living body, and wherein the target area includes only the textile cloth and the two conductors, the textile cloth being located inside and outside the target area.

9. The biological information detection device according to claim 8, wherein the two conductors are set in the textile cloth to satisfy at least one of (a) a first condition that at least one of the two conductors be at least a partial element of a fabric structure of the textile cloth, (b) a second condition that at least one of the two conductors be disposed between layers in the textile cloth having a multi-layered structure, (c) a third condition that at least one of the two conductors be disposed between two layers of the textile cloth or between the textile cloth and another material, (d) a fourth condition that at least one of the two conductors be disposed as a sewing material into the textile cloth, (e) a fifth condition that at least one of the two conductors be disposed at an end of the textile cloth, and (f) a sixth condition that at least one of the two conductors be disposed in the textile cloth as a part of a pattern or a design.

10. The biological information detection device according to claim 8, wherein the two conductors include (a) a carbon material or (b) at least one of a thread with conductive ink and a textile cloth with conductive ink.

11. The biological information detection device according to claim 8, wherein the circuitry is configured to simultaneously determine pulmonary ventilation rate of lungs and number of heartbeats of a heart in the living body as the biological information.

12. An input device comprising:

two conductors that are sewn onto a fiber sheet so as not to be in direct contact with a skin of a measurement target, the two conductors terminating in a predetermined area of the fiber sheet;

circuitry that is connected to the two conductors and is configured to determine an impedance variation in the predetermined area of the fiber sheet based on a voltage value between the two conductors, which are electrically separated from each other at the predetermined area; and a shield that covers portions of the two conductors between the circuitry and the predetermined area so that the portions of the two conductors inside the predetermined area remain uncovered, wherein the shield is configured to be between the covered portions of the two conductors and the measurement target, wherein the predetermined area includes only the fiber sheet and the two conductors, the fiber sheet being located inside and outside the predetermined area, and wherein the circuitry is configured to apply a high-frequency current in a range from 100 kHz to 5 MHz to the predetermined area so that the high-frequency current flows in the measurement target in a contactless manner between the conductors and the skin of the measurement target.

13. The input device according to claim 12, wherein the two conductors are sewn onto the fiber sheet to satisfy at least one of (a) a first condition that at least one of the two conductors be at least a partial element of a fabric structure of the fiber sheet, (b) a second condition that at least one of the two conductors be disposed between layers in the fiber sheet having a multi-layered structure, (c) a third condition that at least one of the two conductors be disposed between two layers of the fiber sheet or between the fiber sheet and another material, (d) a fourth condition that at least one of the two conductors be disposed as a sewing material into the fiber sheet, (e) a fifth condition that at least one of the two conductors be disposed at an end of the fiber sheet, and (f) a sixth condition that at least one of the two conductors be disposed in the fiber sheet as a part of a pattern or a design.

14. A method for acquiring biological information comprising:

providing two conductors that are set in a textile cloth so as not to be in direct contact with a skin of a living body, the two conductors terminating in a target area of the textile cloth;

applying a high-frequency current in a range from 100 kHz to 5 MHz to the two conductors; and determining the biological information based on a voltage value between the two conductors, which are electrically separated from each other at the target area, in a state in which the high-frequency current flows in the living body in a contactless manner between the conductors and the skin of the living body, wherein portions of the two conductors outside of the target area are covered by a shield and the portions of the two conductors inside the target area remain uncovered by the shield, wherein the shield is positioned between the covered portions of the two conductors and the living body, and wherein the target area includes only the textile cloth and the two conductors, the textile cloth being located inside and outside the target area.

15. A biological information detection device comprising:

a first pair of conductors that are set in a textile cloth so as not to be in direct contact with a skin of a living body, the first pair of conductors terminating in a first target area of the textile cloth;

a second pair of conductors that are set in the textile cloth so as not to be in direct contact with the skin of the living body, the second pair of conductors terminating in a second target area of the textile cloth;

circuitry that is connected to the first pair of conductors and the second pair of conductors and is configured to determine biological information based on a voltage value between the first pair of conductors, which are electrically separated from each other at the first target area, or between the second pair of conductors, which are electrically separated from each other at the second target area; and a shield that covers portions of the first pair of conductors outside of the first target area and covers portions of the second pair of conductors outside of the second target area, wherein the shield is configured to be between the covered portions of the first and second pairs of conductors and the living body, wherein the shield does not cover the portions of the first pair of conductors inside the first target area, wherein the shield does not cover the portions of the second pair of conductors inside the second target area, wherein the first target area includes only the textile cloth and the first pair of conductors, wherein the second target area includes only the textile cloth and the second pair of conductors, wherein the textile cloth is located inside and outside the first and second target areas, and wherein the circuitry is further configured to apply a high-frequency current in a range from 100 kHz to 5 MHz to the second pair of conductors so that the high-frequency current flows in the living body at the second target area in a contactless manner between the second pair of conductors and the skin of the living body.

16. A biological information detection device comprising:

a textile cloth having a plate-shape or a sheet-shape with a target area;

at least two conductors that are set in the textile cloth so as not to be in direct contact with a skin of a living body, the at least two conductors terminating at the target area of the textile cloth; and circuitry that is connected to the at least two conductors and is configured to determine biological information based on a voltage value between the at least two conductors, which are electrically separated from each other at the target area; and a shield that covers portions of the at least two conductors outside of the target area, wherein the shield is configured to be between the covered portions of the at least two conductors and the living body, wherein the shield does not cover the portions of the at least two conductors inside the target area, wherein the target area includes only the textile cloth and the at least two conductors, the textile cloth being located inside and outside the target area, and wherein the circuitry is further configured to apply a high-frequency current in a range from 100 kHz to 5 MHz to the at least two conductors so that the high-frequency current flows in the living body at the target area in a contactless manner between the at least two conductors and the skin of the living body.

* * * * *